United States Patent [19]

Grimes et al.

[11] Patent Number: 4,795,634

[45] Date of Patent: Jan. 3, 1989

[54] METHOD FOR CONTRACEPTION BY IMMUNIZATION AGAINST THE ZONA PELLUCIDA

[75] Inventors: Stephen Grimes; Elizer Benjamini, both of Davis, Calif.; Philip Gevas, Honolulu, Hi.

[73] Assignee: Aphton Corporation, Woodland, Calif.

[21] Appl. No.: 839,894

[22] Filed: Mar. 14, 1986

[51] Int. Cl.$^4$ .................... C07K 15/14; A61K 39/395
[52] U.S. Cl. ..................................... 424/85.9; 424/88; 424/105; 530/387
[58] Field of Search .......................... 424/85, 88, 105; 530/387

[56] References Cited

U.S. PATENT DOCUMENTS

| | | | |
|---|---|---|---|
| 3,992,520 | 11/1976 | Gwatkin | 424/85 |
| 4,248,864 | 3/1981 | Jones | 514/15 |
| 4,297,343 | 10/1981 | Bohn et al. | 424/85 |
| 4,526,716 | 7/1985 | Stevens | |
| 4,661,586 | 4/1987 | Levy et al. | 424/85 |
| 4,699,880 | 10/1987 | Goldstein | 530/387 X |

FOREIGN PATENT DOCUMENTS 0142345 5/1985 European Pat. Off. .

OTHER PUBLICATIONS

Biology of Reproduction, 25, 997–1008 (1981), Sacco et al.
Endocrinology, 115, 2418–2432 (1984), Skinner et al.
Gaulton, G. N. et al., Ann. Rev. Immunol. 4 pp. 253–280 (1986).
R. C. Kennedy et al., Bio-Techniques, 3, p. 404, 1985.
R. C. Kennedy et al., Scientific American, 225 pp. 48–56 (1986).
Jean L. Marx, Science, vol. 228, pp. 162–165, Apr. 12, 1985.
D. M. Wood et al., Biology of Reproduction, 25, 439–450 (1981).
T. Mori, et al., Journal of Reproductive Immunology, 8 pp. 1–11 (1985).
B. J. Gulyas, et al., Gamete Research 4: 299–307 (1983).
Y. Noda, et al., Journal of Reproductive Immunology, 3, pp. 147–156 (1981).
R. E. Fowler, et al., Histochemical Journal, 17, pp. 1235–1249 (1985).

*Primary Examiner*—Howard E. Schain
*Attorney, Agent, or Firm*—Dimitrios T. Drivas; Irene J. Frangos

[57] ABSTRACT

This invention relates to a method for contraception comprising the active immunization of a female mammal against zona pellucida using a composition comprising an effective amount of anti-idiotypic antibodies formed against anti-zona pellucida antibodies, which anti-idiotypic antibodies express internal images of zona pellucida antigenic determinants capable of eliciting a contraceptive response.

10 Claims, 2 Drawing Sheets

METHOD FOR CONTRACEPTION BY IMMUNIZATION AGAINST THE ZONA PELLUCIDA

TECHNICAL FIELD OF THE INVENTION

This invention relates to the control of female fertility. More particularly, this invention relates to a method of contraception comprising immunizing a female mammal against the zona pellucida by means of active immunization. According to this invention, anti-idiotypic antibodies to antibodies to the zona pellucida, which express an internal image of an antigenic determinant of the zona pellucida, are administered to a female mammal in order to elicit an active immune response to the zona pellucida and thereby prevent conception.

BACKGROUND OF THE INVENTION

Conventional methods of contraception include the use of mechanical or chemical barriers to fertilization, administration of hormones, or the use of mechanical means to prevent implantation of a fertilized ovum. Typically, these methods have serious drawbacks, including practical inconvenience, incomplete effectiveness and various undesirable side effects. Mechanical means of contraception may cause infection and are often not sufficiently effective. The oral administration of hormones, commonly referred to as "the pill," has been linked to many physiological problems, including various forms of cancer.

In view of the disadvantages of such treatments, efforts have been directed to making use of the body's immune system to prevent conception. For example, immunization against hormones such as follicle stimulating hormone (FSH) or human chorionic gonadotropin hormone (HCG) for the purpose of contraception has been previously reported [U.S. Pat. No. 4,526,716]. However, these methods are also characterized by various side effects.

The zona pellucida ("ZP"), is a glycoprotein matrix encasing mammalian oocytes which plays an important role in the reproductive process. Its primary functions include the binding of sperm through its sperm-binding receptors, the prevention of polyspermy following fertilization, and the protection of the zygote until ZP shedding immediately prior to implantation. One method of reproduction control comprises denuding a blastocyte by removing its ZP [U.S. Pat. No. 4,248,864].

Purified ZP is an efficient immunogen, evoking high levels of specific antibodies when injected into species other than the one from which the ZP preparation was derived. Methods of contraception have been developed which rely on the fact that, when females are immunized with ZP, the elicited antibodies to ZP are capable of preventing pregnancy [U.S. Pat. No. 3,992,520].

The effectiveness of treatments involving the use of purified ZP, however, has been limited by a variety of factors, including the need for the large amount of purified protein necessary to elicit the immune response. The purification of ZP, which is time-consuming and expensive, has made such contraceptive methods which require large amounts of pure ZP impractical.

In addition, immunizing with purified whole ZP, or any of its major subunits, elicits heterogeneous antibody populations directed against the numerous antigenic determinants expressed by ZP. Many of the antibodies thus elicited may be irrelevant to effective contraception. Studies have shown that certain monoclonal anti-ZP antibodies are not contraceptive [D. W. Drell and B. S. Dunbar, "Monoclonal Antibodies To Rabbit And Pig Zona Pellucide Distinguish Species—Specific And Shared Antigenic Determinants," *Biology Of Reproduction,* 30 p. 445 (1984)]. This approach allows for no control over the specificity of the anti-ZP antibodies thus elicited, and may be not only wasteful but also harmful. It has been demonstrated in experiments with rabbits that immmunization with whole ZP can result in serious negative side effects, including alterations in follicular cell differentiation accompanied by abnormally elevated serum gonadotropin levels [J. M. Skinner et al., "Immunization With Zona Pellucida Proteins Results In Abnormal Ovarian Follicular Differentiation An Inhibition Of Gonadotropin-Induced Steroid Secretion," *Endocrinology* 115, p. 2418 (1984)].

SUMMARY OF THE INVENTION

The present invention provides a method of contraception comprising immunizing female mammals with anti-idiotypic antibodies to anti-ZP antibodies, i.e., antibodies which express "internal images" of the antigenic determinants of ZP. The method of the present invention involves eliciting ZP-specific antibodies by administering to a female mammal a composition comprising a contraceptive effective amount of anti-idiotypic antibodies to ZP.

The present invention also relates to anti-idiotypic antibodies which are useful in the foregoing methods of contraception, particularly when used to prepare a contraceptive composition for administration to female mammals.

DETAILED DESCRIPTION OF THE INVENTION

Figure 1:
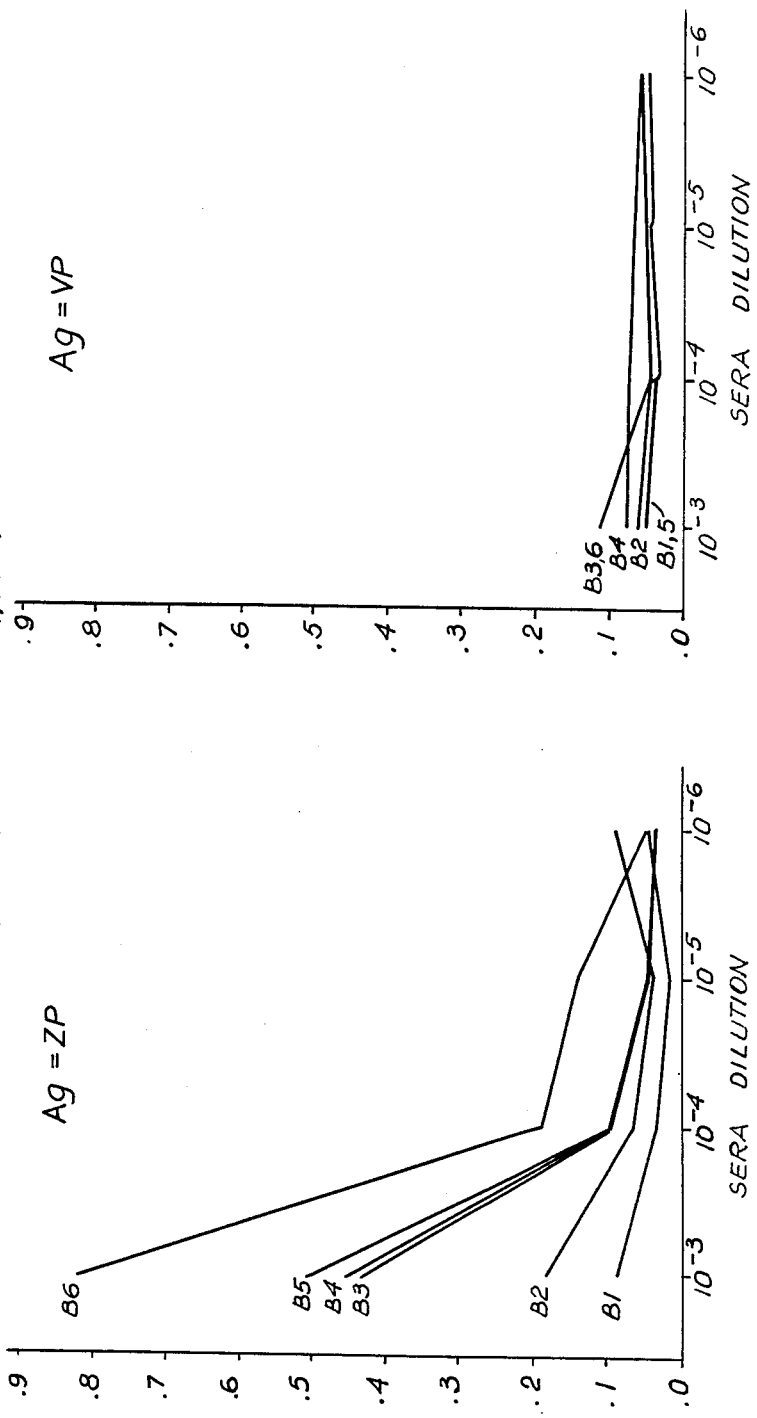

In order that the invention herein described may be more fully understood, the following detailed description is set forth. In the description, the following terms are employed:

ZONA PELLUCINDA (ZP)—The zona pellucida is a tough, refractile, extracellular glycoprotein matrix enveloping the oocyte. Its characteristic striated appearance results from the numerous fine canals with which it is pierced. Cytoplasmic processes from the follicular cells extend through the ZP and occasionally invaginate the plasma membrane of the oocyte. The cytoplasmic processes of the follicular cells also transport nutritive material to the surface of the oocyte. In addition, microvilli of the oocyte extend into the ZP and increase the absorptive capacity at the surface of the oocyte. [See, generally, W. J. Hamilton, ed., *Hamilton, Boyd and Mossman's Human Embryology,* pp. 27–32 and 54–64 (1972); J. B. Warshaw, ed., *The Biological Basis Of Reproduction And Developmental Medicine* (1973).]

As used in this application, "ZP" includes all forms of the glycoprotein matrix which are capable of eliciting antibodies to ZP. These encompass ZP epitopes which appear late in an oocyte's development, during the antral and preovulatory phases, as well as epitopes which are expressed after ovulation.

The term "ZP", as used herein, includes whole ZP extract, the three individual glycoprotein fractions which comprise ZP, any enzymatically digested or chemically denatured forms of ZP, or any combinations thereof. In addition, "ZP" includes isolated ZP antigenic determinants which are not inherently immunogenic but which can be utilized as immunogens when they are chemically linked to immunogenic carrier molecules (e.g., Keyhole Limpet Hemocyanin, Diptheria Toxoid, etc.).

ANTI-IDIOTYPE—The hypervariable region of an antibody has the capacity to act as an antigenic determinant (epitope). Antibodies directed to this region of the immunoglobulin molecule may be highly specific. This antigenic determinant that induces antibody formation is referred to as the idiotypic determinant, or idiotype, and the anti-antibodies it elicits are referred to as anti-idiotypes ("anti-id"). [see A. Nisonoff, *Introduction To Molecular Immunology* (1984); J. Oudin and M. Michel, "Une nouvelle form d'allotypic des globulins γ du sérum de lapin, apparemment lieé à la fonction et à la specificité anticorps," *Compt. Rend. Acad. Sci (Paris)*, 257, p. 805 (1963)].

Anti-idiotypic antibodies can express an "internal image" of the epitope against which the original antibody was formed. Thus, such anti-id antibodies combine with the antibody's binding site [see, E. S. Golub, *The Cellular Basis of the Immune Response*, pp. 178–179 (1979)].

INTERNAL IMAGE—An epitope, expressed by an antibody, that shares immunologic crossreactivity with an antigenic determinanant expressed by some other (generally external) antigenic molecule.

MONOCLONAL ANTIBODIES—Monoclonal antibodies are obtained by fusing an antibody-producing cell, which secretes a single species of antibody molecule, with a myeloma tumor cell. A cell line is then propagated from the fused cell line. The fused cell line, referred to as a hybridoma, has the characteristic immortality of a tumor cell line, and secretes the desired antibody in large amounts. Hybridomas, which can be made according to the methods of G. Kohler and C. Milstein ["Continuous Cultures of Fused Cells Secreting Antibodies of Predefined Specificities," *Nature*, 256, p. 495, (1975)], are a major source of homogeneous antibodies. Unlimited amounts of monoclonal antibodies formed in this manner can be prepared against the desired antigens or haptens [See, C. Milstein, "Monoclonal Antibodies," *Scientific American*, 243, p. 66, (1980); A. Nisonoff, *Molecular Immmunology* (2d Edition), pp. 169–181, (1984)].

ACTIVE IMMUNIZATION—The process of eliciting a humoral immune response to an antigen or hapten, as opposed to supplementing the body's immune system by adding antibodies formed to that antigen or hapten (i.e., passive immunization).

This invention relates to a method for contraception comprising the step of administering to a female mammal a composition comprising a contraceptive effective amount of anti-idiotypic antibodies to anti-zona pellucida antibodies. The aforementioned anti-idiotypic antibodies may be obtained by the production of polyclonal or monoclonal antibodies against ZP's antigenic binding sites (epitopes) followed by the use of these antibodies to elicit anti-antibodies. These anti-antibodies possess antigenic determinants which immunochemically crossreact with similar antigenic determinants on ZP. The portion of the anti-antibodies which are capable of binding to the anti-ZP antibodies' antigen binding sites possess internal images of the ZP determinants against which the anti-ZP antibodies are directed.

Advantageously, the method of this invention allows for the production of antibodies by the female mammal against anti-id antibodies expressing internal images of the antigenic determinants of ZP. These anti-id antibodies are used in place of the actual antigen as a means to elicit ZP-specific antibodies and thereby prevent conception. The present invention provides a distinct advantage over immunization with whole ZP, or its subunits, which elicits heterogeneous antibodies directed against the multitude of antigenic determinants expressed by ZP. The internal image vaccines of this invention allow for the precise regulation of the heterogeneity of the anti-ZP response, and demonstrate no potentially harmful side effects. Furthermore, internal image vaccines of this invention can be inexpensively produced in large quantities needed for vaccination programs.

The ZP used in the method of this invention can be taken from any stage in the development of the oocyte. Certain ZP epitopes are temporally expressed as oogenesis proceeds. For example, certain epitopes appear during the antral and preovulatory phases of an oocyte's development, and other epitopes are are expressed during and after ovulation.

In a preferred embodiment of the present invention, the anti-idiotypic antibodies are directed against ZP epitopes which develop late in oogenesis, or immediately after ovulation ("late ZP epitopes") rather than those expressed during the earlier stages of oocyte development. Antibodies specific for late ZP epitopes do not react with ZP associated with earlier stages of oocyte development. The antibodies elicited to late ZP epitopes are capable of binding to their targets for only a short time before exiting the ovary upon ovulation. Thus, any potential negative side effect of bound ZP-antibody complex in the ovary is minimized, while effective contraceptive activity is provided.

According to one embodiment of this invention, the appropriate ZP preparation is used to immunize mice whose anti-ZP antibody levels are assayed by standard serological procedures. When anti-ZP antibody titers have reached acceptable levels, the anti-ZP antibodies are tested for their ability to block in vitro or in vivo conception in the target species. Cells from mice whose antibodies which block fertilization are then used to produce hybridomas. ZP specific monoclonal antibodies are selected and monoclonal cell lines secreting anti-ZP antibodies are established. The monoclonal anti-ZP immunoglobulins are subsequently screened for contraceptive potential on the basis of their ability to block in vitro or in vivo fertilization. Mouse monoclonal antibodies which are contraceptive in the targeted species are then used to elicit anti-antibodies which express internal images of ZP antigenic determinants (see Example 1, infra,). When mice are to be immunized with anti-ZP monoclonal antibodies, the monoclonal antibodies should be coupled to an immunogenic "carrier" protein to enhance immunogenicity; this is not required when immunizing other species with mouse immunoglobulins. Animals which have been immunized with anti-ZP and which show a positive titer may subsequently be used for the production of serum anti-idiotypic antibodies by further immunization and bleeding. Mice and rats may also serve as antibody producing cell donors for the production of monoclonal anti-idiotypic antibodies derived by standard hybridoma techniques.

The choice of species in which to raise the anti-idiotypic antibodies is dictated by the intended use of the antibodies. If one desires to produce monoclonal anti-idiotypic antibodies expressing internal images, mice and rats are the preferred species. If it is intended that sera serve as the source of anti-idiotypic antibodies, larger animals (e.g., horses or swine) are preferable since they yield greater quantities of sera. To prepare vaccines for use in humans, dogs, cats or other large mammals, large species, such as burrows, horses or goats are preferable. It is preferable to generate the internal images in species other than the one to be immunized, so that there is not need to couple the internal image antibodies to an immunogenic carrier in order to generate an immune response.

The method of this invention may be used to treat any mammal, including, but not limited to, dogs, rabbits, rats, mice, pigs or primates, including humans. Anti-idiotypic antibodies to anti-ZP antibodies that are effective in preventing contraception in a particular species of mammals may not be contraceptive in all mammals. This is due to antigenic differences in the ZP of different species. For example, immunization with porcine ZP will prevent conception in dogs, rabbits and various primates (e.g., cynomolgus monkeys), but not in rats or mice because, although rats and mice produce antibodies to porcine ZP, the antibodies do not cross react with rat or mouse ZP. In view of the foregoing, it will be understood that in practicing the method of the present invention, the initial immunogen ZP must be capable of eliciting contraceptive antibodies that can react with the ZP of the species targeted for fertility control. The ZP may be obtained from the target species or from an appropriate alternative species.

The contraceptive capacity of the anti-idiotypic antibodies obtained, as described above, may be tested in the target species as follows: the animals are immunized with purified or partially purified preparations of anti-idiotypic antibodies expressing internal images of one or more ZP antigenic determinants and the anti-ZP antibody titers are monitored. When titers reach acceptable levels, the anti-ZP antibodies are tested for their ability to inhibit in vitro or in vivo fertilization in the target species. Anti-idiotypic antibodies which elicit anti-ZP responses in the target female effectively prevent conception when they are used to prepare a contraceptive vaccine. Each dose of the vaccine should contain an amount of anti-idiotypic antibodies that will elicit the production of a quantity of anti-ZP antibodies sufficient to elicit a contraceptive effect in a female of the target species.

The means by which anti-ZP antibodies prevent conception has not been thoroughly established. Without being bound by theory, we believe that the contraceptive effect of our vaccine is due to the steric hindrance around the zona pellucida, which prevents a sperm from passing through the ZP to fertilize the ovum. When the antibodies formed to the ZP attach themselves to the ZP epitope, the sperm is physically unable to penetrate through the zona pellucida. Possible other mechanisms include alterations in normal ovarian functions. When anti-ZP antibody levels recede following the cessation of immunization procedures, fertility is regained.

A vaccine of this invention may be either monovalent of multivalent. That is, it may comprise a single monoclonal antibody species that expresses a single internal image of ZP, or it may comprise a mixture of monoclonal antibody species, each of which expresses an antigenically distinct internal image of ZP. Additionally serum antibodies may be used to elicit the contraceptive anti-ZP response.

Administration of these anti-idiotypic antibodies, or pharmaceutically acceptable derivatives thereof, may be via any of the conventionally accepted modes of administration of agents which exhibit immunogenicity against ZP epitopes. These include various parenteral routes, including, but not limited to, subcutaneous, intramuscular, intraperitoneal, and intravenous administrations.

The compositions used in these therapies may also be in a variety of forms. The anti-idiotypic antibodies, which will generally be administered using the foregoing methods, also will preferably include conventional pharmaceutically acceptable carriers typically used in vaccine formulations, such as sterile water or sterile saline solution. Vaccine compositions comprising the anti-antibodies may also include other medicinal agents, adjuvants, excipients, etc. Preferably, the compositions of this invention are in the form of a unit dose. The amount of anti-idiotypic antibodies administered as a vaccination at one time, or over a period of time, will depend on the subject being treated, the manner and form of administration, and the judgment of the treating physician or veterinarian. However, an contraceptively effective dose may be in the range of from about 1 ng/kg to about 1 mg/kg, preferably about 10 $\mu$g/kg to about 100 $\mu$g/kg; it being recognized that lower and higher doses may also be useful. Generally, one such dose of vaccine is expected to provide a contraceptive effect for a period of about six months. Accordingly, after the initial immunization, it is desirable to provide immunizations approximately every six months.

In order that the invention described herein may be more fully understood, the following examples are set forth. It should be understood that these examples are for illustrative purposes only and are not to be construed as limiting this invention in any manner.

EXAMPLE I

Demonstration That ZP Internal Image Antibodies Elicit Anti-ZP Response

We produced monoclonal anti-ZP antibodies from mice immunized against porcine ZP. We chose porcine ZP because of its multi-species cross reactivity. In order to create our ZP antigens, we heated solubilized porcine ZP, deglycosylated the porcine ZP, and isolated the 90 kd, 65 kd, and 55 kd molecular weight fractions of porcine ZP according to the methods of D. W. Drell and B. S. Dunbar [*Biology of Reproduction*, 30, p. 445 (1984)].

We generated ZP-specific monoclonal antibodies by injecting four one-month old female CAF$_1$ mice intraperitoneally with 70–100 $\mu$g porcine ZP emulsified in FCA (H37 Ra), the standard oil-based adjuvant used in immunological studies in mice. We gave subsequent injections at four week intervals. Each injection consisted of 100 $\mu$g ZP in saline administered intraperitoneally. Epinephrine (0.1 ml) (1:5000) was injected intraperitoneally with each ZP (saline) boost. We thus elicited the production of antibodies specific for whole ZP, deglycosolyated ZP, the 90 kd, 65 kd and 55 kd fractions of whole ZP, and carbohydrate epitopes expressed by ZP.

In order to ascertain whether the mice were producing ZP-specific antibodies, we conducted an Enzyme-Linked Immunosorbent Assay ("ELISA"). In this assay, the antibody is labelled by a covalently attached enzyme (instead of the radiolabel used in a radioimmunossay). The enzyme attached to the antibody is one that can react with a colorless substrate to give a colored product. The amount of product released in a fixed period of time depends on the concentration of enzyme, and this in turn is a measure of the amount of antibody present. Specialized spectrophotometric equipment reads the optical densities (O.D.), which correlates with the amount of bound antibody.

We established our assay, as follows: we coated Immulon ® (made by Dynatech) II U-Plate wells with 25 μl antigen in solution of coating buffer (0.1M glycine, pH=9.5) (ZP, deglycosylated ZP, 90 kd, 65 kd, or 55 kd proteins) at 2-10 μg/ml in glycine buffer (0.1M, pH=9.5) and maintained the coated wells overnight at 4° C. The wells were rinsed four times with a wash solution of saline to which we had added 0.5% Tween-20 and 0.02% $NaN_3$. We then added 25 μl of primary antibodies (ten-fold serial dilutions of anti-ZP sera obtained from mice immunized with whole ZP, running from $10^{-1}$ through $10^{-8}$, or cell culture supernatants) per well and incubated for one hour at 22° C. We then rinsed the wells again. We followed these by 25 μl of secondary antibodies per well, consisting of either rabbit anti-mouse Ig (polyspecific or monospecific isotyping reagents, diluted with FTA Hemagglutination Buffer+0.05% Tween-20+0.02% $NaN_3$ 1:1000) or biotinylated rabbit anti-mouse Ig (1:1000) and incubated for one hour at 22° C. We again rinsed the wells and then added to each well 25 μl of either goat anti-rabbit Ig-alkaline phosphatase conjugate (1:2000) or avidin-alkaline phosphatase conjugate (1:1000) and incubated for one hour at 22° C. We then rinsed the wells again. We again rinsed the wells, and we then added to each well, 25 μl of 1 mg/ml p-nitrophenyl-phosphate (in 10% diethanolaine, 0.5 mM $MgCl_2$, 0.02% $NaN_3$, pH=9.8) and allowed the color to develop for 5-30 minutes. We determined the optical densities with a Dynatech Microelisa Reader. Our diluting solution consisted of FTA Hemagglutination buffer (pH=7.2) to which we added 0.05% Tween-20 and 0.02% $NaN_3$. We coated other protein antigens, such as hen egg lysosome, bovine serum albumin, and chicken ovalbumin, as negative controls for antibody specificities, onto plates and analyzed them in a manner similar to that described above.

We performed ELISAs on 1:10 serial dilutions of serum obtained via tail vein bleedings of ZP immunized mice using our dilution solution. Our assays demonstrated that out immunization protocols routinely evoked anti-ZP titers equal to or exceeding $10^5$ within 7 days of the second injection of antigen. Our assays also demonstrated that immunization with ZP elicited antibodies directed against conformational antigenic determinants expressed by heat solubilized ZP, carbohydrate specific determinants, and determinants expressed by the 90 kd, 65 kd, and 55 kd fraction isolates. Accordingly, our immunization procedure elicited antibodies specific for all of our ZP-antigen preparations. Thus, cells obtained from those mice could be used as fusion partners to obtain hybrids secreting antibodies against various ZP-antigen preparations.

We then performed cell fusions according to the methods of B. B. Mishell and S. M. Shiigi [Selected Methods in Cellular Immunology, San Francisco (1980)]. We created hybridomas producing monoclonal anti-ZP antibodies by fusing spleen cells from ZP immunized mice with P3 tumor cells using polyethylene glycol. We selected our hybrids by feeding on Hypoxanthine-Aminopterin-Thymidine [HAT] supplemented media and then screening for specific antibody production by ELISA. Two fusions (F123 and F286) each yielded several distinct hybridoma lines. Hybrids obtained from fusion 123 were derived from mice which had been reexposed to ZP to elevate their existing immune response (ZP-boosted) and selected through their reactivities against ZP using the ELISA protocol defined above. After the hybrid lines were established, we confirmed that our hybrids were secreting monoclonal antibodies against various ZP antigen preparations, including whole ZP, deglycosylated ZP, the 55 kd and 90 kd fractions thereof, and carbohydrate determinants of ZP. Hybrids from fusion 286 were derived from mice boosted with a mixture of ZP, 90 kd, and 65 kd fractions. We considered cell lines to be established when their cloning efficiencies reached 100%. Samples of established cell lines were frozen and stored under liquid $N_2$.

We generated working quantities of monoclonal antibodies as ascites tumors in the peritoneal cavities of mice and collected the ascites fluid, according to the methods of Mishell, supra. We injected $CAF_1$ mice with 0.5 ml of Pristane, intraperitoneally. Three days later, we injected $2 \times 10^6$ hybrid cells, suspended in 0.5 ml saline, into the mice intraperitoneally. After collecting the ascites fluid from the peritoneal cavity of the ascites fluid from the peritoneal cavity of mice, we centrifuged the fluid (400 xg. for 10 minutes, to remove the cells.

Referring now to Table I, we have listed therein the monoclonal antibodies that we obtained as described above, along with their isotypes and specificities. We determined the isotypes of ELISA as described above, and determined the specificities on the basis of reactivities against ZP and the various ZP components in ELISAs. We verified this data by Western blot analysis according to known methods [see, e.g., Drell, supra].

TABLE I

| Cell line/Antibody | Isotype | Specificity |
|---|---|---|
| 123-3 | IgG-1 | 90 Kd |
| 123-5 | IgG-1 | conf.* |
| 123-7 | IgG-1 | conf. |
| 123-8 | IgG-3 | CHO** |
| 123-11 | IgG-1 | conf. |
| 123-12 | IgG-1 | 55 Kd |
| 123-13 | IgG-1 | conf. |
| 286-1 | IgM | CHO |
| 286-2 | IgG-1 | 90 Kd |
| 286-3 | IgG-1 | 90 Kd |
| 286-4 | IgG-1 | 90 Kd |
| 286-5 | IgG-1 | 90 Kd |
| 286-6 | IgG-1 | 90 Kd |
| 286-7 | IgG-2a | 90 Kd |
| 286-8 | IgA | 90 Kd |

*conf. = conformational determinant lost when heat solubilized ZP separated into constituent fraction.
**CHO = carbohydrate dependant determinants, lost with deglycosylation.

We assessed the capacity of the monoclonal antibodies to bind to oocyte-associated ZP from freshly sectioned porcine oocytes via immunofluorescence using the procedure of I. J. East and J. Dean [Journal of Cell Biology, 98, p. 795 (1984)]. All the monoclonals we screened (i.e. the 123 series) were shown to bind oocyte associated ZP, thus demonstrating the reactivity of the antibodies produced.

Generation Of Anti-idiotypic Antibodies Directed Against The Anti-ZP Monoclonal Antibodies A. Generation of Anti-Idiotypic Antibodies In Mice We prepared our immunogen by chemically coupling our monoclonal antibodies from fusion 123 to keyhole limpet hemocyanin ("KLH"), an immunogenic protein, using equal amounts of antibodies and KLH.

We isolated KLH, purchased as an ammonium sulphate haemolymph precipitate, by dialysis of the precipitate slurry, against 0.5.M NaCl followed by gel filtration over a Sephacryl® 400 column (50×1.5 cm, 3 ml/hour, 1M NaCl). We pooled KLH containing fractions and determined the protein concentrations using standard spectrophotometric techniques using a Gilford Spectrophotometer #260 (A280 measurements) and dialyzed the combined material against 0.5m NaCl. We then concentrated the dialyzed material to 5 mg/ml on an Amicon concentrator.

We combined equal volumes of 123-3, 123-5, 123-7, 123-8, 123-11, 123-12, and 123-13 ascites fluids (titers within one tenfold order of magnitude as determined by ELISA). In order to purify our monoclonal antibody mixture, we precipitated it with ammonium sulphate (40%), dialyzed the precipitate against $H_2O$ and then lyophilized the dialyzed solution. We dissolved 10.0 mg of the lyophilized 123 antibody mix in 2.5 ml 0.5M NaCl containing 5.0 mg KLH. After centrifuging the mixture to remove a small amount of insoluble material (10 minutes at 2000×g), we added 50 mg of 1-ethyl-3-(3-dimethylaminopropyl) carbodiimide hydrochloride while stirring. We allowed the reaction to proceed for 16 hours at room temperature and then dialyzed the mixture against 0.5M NaCl. We froze the dialyzed mixture, stored it, and thawed it just prior to use.

We immunized $CAF_1$ mice with 0.1 ml injections (containing 100 μg of conjugate per injection) by a protocol identical to that described supra, for immunization against ZP. We obtained serum via tail vein bleedings at various intervals following injections.

We assayed the sera we had obtained to determine the presence of mouse anti-idiotypic antibodies on the basis of their ability to block the binding of anti-ZP monoclonal antibodies (123 monoclonals) to ZP. We diluted pooled serum from 123-immunized mice to $1:10^2$ with ELISA diluting buffer and then mixed the diluted serum 1:1 samples of anti-ZP monoclonal antibodies diluted to $1:10^4$, $10^5$, or $10^6$. These samples included the ammonium sulphate-precipitated 123 mix, as well as each of the individual (ascites) monoclonals which comprised the mix. After incubating each mixture for one hour at room temperature, we added 25 μl of each mixture to ZP-coated ELISA plate wells. Following this, we followed the standard ZP ELISA protocol to ascertain anti-ZP specificities. As controls we included samples of both anti-id sera and monoclonal antibody preincubated with normal mouse sera at the appropriate dilutions.

Table II depicts the degree of blocking activity of mouse anti-id sera, as the percent inhibition of the binding of anti-ZP monoclonal antibodies to ZP.

TABLE II

| | anti-Zp (at $1:10^4$ dilution) | | | | | | | |
|---|---|---|---|---|---|---|---|---|
| | mix | 123-3 | 123-5 | 123-7 | 123-8 | 123-11 | 123-12 | 123-13 |
| Percent Inhibition | 37 | 10 | 79 | 47 | 18 | 20 | 22 | 18 |

As shown in Table II, the anti-idiotypic sera inhibited the binding of the mixture of monoclonals from fusion 123 by 37%. This indicated the presence of id-specific antibodies in the sera. We then tested the ability of the anti-idiotypic sera to inhibit individual monoclonal antibodies by ascertaining the degree to which each of the individual monoclonal antibodies had been inhibited. Antibody 123-5 was inhibited by 79% and antibody 123-7 by 47%. The high degree of inhibition obtained against 123-5 and 7 suggests a strong anti-id response. Relatively weak responses were elicited by 123-8, 123-11, 123-12 and 123-13. Essentially no anti-ids were evoked by 123-3. Our data confirmed that our sera contained high anti-idiotypic antibody titers against some of the individual monoclonal antibodies in the mixture.

B. Generation Of Anti-Idiotypic Antibodies In Rabbits

We immunized a rabbit with 0.5 mg of the previously described mixture of monoclonal antibodies from fusion 123 which has been dissolved in saline. We coprecipitated the 1.0 mg of the antigen onto alum and injected a total volume of 0.5 ml subcutaneously into the rabbit's back [see Mishell and Shiigi, supra, p. 47]. We administered an identical injection one month after the first injection. Subsequent injections, each consisting of 1.0 mg antigen in saline, were given at monthly intervals. We obtained serum samples from central ear artery bleedings.

We assayed rabbit sera samples for the presence of anti-id activity via inhibition ELISAs. The assays were performed in a manner identical to that described for the determination of mouse anti-id activity, except that 1% normal mouse sera was included in the diluting buffer (to absorb out rabbit anti-mouse Immunoglobulin ("Ig") activity unrelated to the 123 idiotypes). Table III depicts the percent inhibition by rabbit anti-idiotypic sera of anti-ZP monoclonal antibodies binding to ZP.

TABLE III

| | anti-ZP (at $1:10^5$ dilution) | | | | | | | |
|---|---|---|---|---|---|---|---|---|
| | mix | 123-3 | 123-5 | 123-7 | 123-8 | 123-11 | 123-12 | 123-13 |
| Percent Inhibition | 74 | 63 | 81 | 72 | 38 | 36 | 12 | 46 |

As the data in Table III indicate, the rabbit sera were capable of inhibiting the binding of the 123-mix by 74%. This can be explained by the high titers of antibody contained in the rabbit sera. We then checked the rabbit sera's ability to inhibit individual monoclonal antibodies. Strong anti-id responses were elicited against 123-3, 123-5, and 123-7, moderate activity was directed against 123-8, 11 and 13, while a relatively weak response was evoked by 123-12. Accordingly, against all but one of the monoclonals, the rabbit sera responded well.

Elicitation Of Anti-ZP Antibodies In Rabbits And Mice By Immunization With Anti-Idiotypic Antibodies We next elicited anti-ZP antibodies in rabbits and mice through immunization with the anti-idiotypic antibodies.

A. Immunization Of Rabbits With Mouse Anti-Idiotypic Antibodies

We immunized a rabbit with mouse anti-idiotypic antibodies using the serum we had generated as described above under Generation . . . in Mice. We precipitated the mouse serum containing anti-id activity against 123 monoclonal antibodies with the addition of saturated ammonium sulphate, to a final ammonium sulphate concentration of 40%. We then redissolved the precipitate in 5.0 ml FTA hemagglutination buffer and dialyzed against the same buffer. We emulsified 1.0 mg of this preparation in FCA and injected 0.2 ml subcutaneously into a rabbit's back. Subsequent innoculations were administered in saline at monthly intervals at the same site. We injected 1.0 mg antigen in the first booster and 2.0 mg antigen in the second. Blood was periodically drawn from the rabbits' central ear arteries. We bled the rabbits 14 and 32 days after the first injection. We gave a second injection on the 32nd day and bled the rabbit on days 40, 54 and 62. The third injection was given on day 68 and the rabbit was bled again on day 83.

We assayed serum samples at ten-fold serial dilutions using the standard ZP ELISA. Nonspecific binding was checked against a viral protein (VP) antigen, immunologically unrelated to ZP; negative control sera were obtained from a rabbit immunized with ammonium sulphate precipitated ascites fluid containing antibodies not directed aganist ZP. As can be seen from FIG. 1, anti-ZP antibody levels progressively increased with successive bleedings, and rose dramatically following the third injection (in which the antigenic dose was doubled). Accordingly, the antibody titer increased as a result of the immunization with anti-idiotypes.

Non-specific binding against VP remained relatively constant. A marginal rise in anti-ZP activity of unknown specificity was detected in the control animal's sera. We verified the presence of anti-ZP activity in the mouse anti-id immunized rabbits sera by indirect immunofluorescence studies utilizing freshly sectioned porcine oocytes. Our control sera was negative. Accordingly, we verified our previous ELISA results, thus adding further evidence that we had elicited anti-ZP antibodies. In addition, we demonstrated that anti-ZP antibodies from an anti-idiotype-immunized rabbit, could bind to ZP as it exists in vivo.

To assess the specificity of the anti-ZP antibodies elicited by mouse anti-id, we assayed the rabbit sera at various dilutions against the various ZP antigen preparations. Table IV depicts the ELISA O.D.'s which indicate the reactivity against ZP, of rabbit sera from the fifth bleeding, diluted 1:10³ with ELISA diluting buffer.

TABLE IV

| Antigen ZP | deglycos. ZP | 90K | 65K | 55K | background* |
|---|---|---|---|---|---|
| O.D. 0.153 | 0.397 | 0.054 | 0.061 | 0.081 | 0.045 |

*background = baseline O.D., obtained using sera taken from a negative control rabbit.

As shown in Table IV, significant reactivity was obtained only against ZP and deglycosylated ZP, suggesting that the mouse anti-id sera elicited rabbit antibodies specific for conformational determinants.

B. Immunization Of Mice With Rabbit Anti-Idiotypic Antibodies

We immunized mice with rabbit anti-idiotypic antibodies using the serum we had generated as described, just above. We precipitated rabbit serum containing anti-id activity directed against 123 monoclonal antibodies with saturated ammonium sulphate added to a final concentration of 40%, and then dissolved in 5 ml FTA hemagglutination buffer and then dialyzed it against FTA hemagglutination buffer. Rabbit antibodies specific for non-idiotypic mouse Ig determinants were removed by passing (twice) over a mouse Ig-Sepharose CL-48 column (column vol=7 ml, running buffer=FTA, 0.5 ml/minute). We verified the removal of rabbit antibodies specific for mouse immunoglobulin determinants not associated with the anti-ZP idiotypes and retention of anti-id blocking activity by ELISA. The anti-id antibodies were concentrated on an Amicon apparatus to 6 mg/ml.

Figure 2:
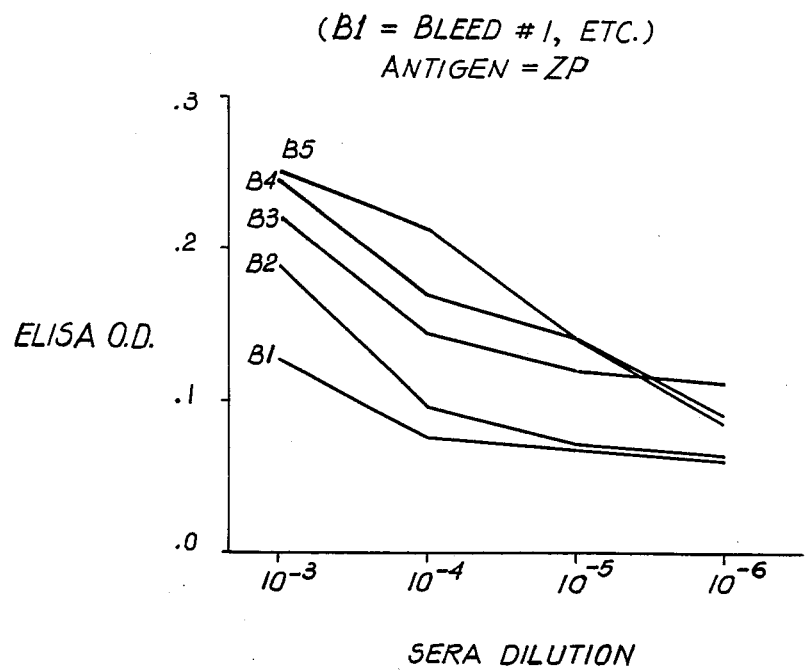

We immunized six one-month old female $CAF_1$ mice with an initial injection of 330 μg rabbit anti-id (FCA) intraperitoneally. After the initial injection, we gave three additional injections. The second and third injections, administered at monthly intervals, contained 100 μg antigen in FTA, given intraperitoneally with 0.1 ml epinephrine (1:5000). In a fourth injection, we gave the mice various dosages (1 μg, 100 μg, or 1 mg). We obtained serum samples by periodic tail vein bleedings [see FIG. 2]. The mice were bled and injected on day 0. On day 31 they received a second injection and were bled on days 42 and 56. They received their third injection on day 57 and were bled on day 67. We administered their final injection on day 74 and bled them 10 days later.

We assessed anti-ZP titers by standard ZP ELISA. We used VP as a negative control antigen. As can be seen from FIG. 2, the rabbit anti-id antibodies elicited anti-ZP responses in mice which continued to increase with subsequent innoculation. Anti-VP antibody levels remained unchanged throughout the course of immunization. Accordingly, the mean antibody level, which we ascertained by ELISA O.D., showed a marked increase as a result of immunization with anti-idiotypic antibodies.

We verified our results by demonstrating that the post-immunization mouse sera contained antibodies which bound to the ZP in freshly sectioned porcine oocytes, using the indirect immunofluorescence technique described by Mishell and Shiigi, supra, p. 299. We treated washed porcine oocytes with 1:40 dilution of mouse antisera (on FTA hemagglutination buffer) for one hour at 22° C. The oocytes were washed (in FTA), then exposed to a 1:100 dilution of fluorescent-rabbit anti-mouse immunoglobulin reagent for one hour at 22° C. Finally, we washed and examined the oocytes by flourescent microscopy.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A method of contraception comprising the step of administering to a female mammal a composition comprising a contraceptive effective amount of anti-idiotypic antibodies formed against anti-zona pellucida antibodies, which anti-idiotypic antibodies express internal images of zona pellucida antigenic determinants capable of eliciting a contraceptive response.

2. The method according to claim 1, wherein the anti-idiotypic antibodies which are used to elicit the contraceptive anti-zone pellucida response are monoclonal antibodies.

3. The method according to claim 1, wherein the anti-idiotypic antibodies which are used to elicit the contraceptive anti-zone pellucida response are serum antibodies.

4. The method of claim 1, wherein the anti-idiotypic antibodies express internal images of ZP antigenic determinants formed immediately prior to or after ovulation.

5. The method according to claim 1, wherein the composition is administered at a dosage of from about 1 ng/kg to about 1 mg/kg.

6. The method according to claim 5, wherein the dosage is about 10 µg/kg.

7. A contraceptive composition, comprising a contraceptive effective amount of anti-idiotypic antibodies to anti-zona pellucida antibodies, which anti-idiotypic antibodies express internal images of zona pellucida antigenic determinants capable of eliciting a contraceptive response, and a pharmaceutically acceptable carrier.

8. The composition according to claim 7, wherein said amount is between about 1 ng/kg and about 1 mg/kg.

9. The composition according to claim 7, wherein said amount is about 10 µg/kg.

10. The use of a contraceptively effective amount of anti-idiotypic antibodies to anti-zona pellucida antibodies, which anti-idiotypic antibodies express internal images of zona pellucida antigenic determinants capable of eliciting a contraceptive response, for the production of a pharmaceutically acceptable composition for contraception.

* * * * *